United States Patent [19]

Lendle et al.

[11] Patent Number: 4,810,798

[45] Date of Patent: Mar. 7, 1989

[54] RECOVERY OF PYRIDINE OR METHYLPYRIDINES OR MIXTURES THEREOF FROM METHYL BUTANEDICARBOXYLATE CONTAINING REACTION MIXTURES

[75] Inventors: Hubert Lendle, Ludwigshafen; Paul Panitz, Worms; Wilfried Seyfert, Weisenheim; Peter Stops, Altrip, all of Fed. Rep. of Germany

[73] Assignee: BASF Aktiengesellschaft, Ludwigshafen, Fed. Rep. of Germany

[21] Appl. No.: 119,493

[22] Filed: Nov. 12, 1987

[30] Foreign Application Priority Data

Nov. 25, 1986 [DE] Fed. Rep. of Germany ....... 3640296

[51] Int. Cl.$^4$ .......................................... C07D 213/06
[52] U.S. Cl. .................................................. 546/353
[58] Field of Search ........................................ 546/353

[56] References Cited

U.S. PATENT DOCUMENTS 4,256,909 3/1981 Kummer et al. .................... 560/204

Primary Examiner—Alan L. Rotman
Assistant Examiner—J. Richter
Attorney, Agent, or Firm—Keil & Weinkauf

[57] ABSTRACT

Pyridine or methylpyridines or mixtures thereof are recovered from methyl butanedicarboxylate containing reaction mixtures obtained by reaction of methyl pentenoate with carbon monoxide and methanol in the presence of pyridine, methylpyridines or mixtures thereof and also cobalt catalysts at elevated temperatures and under superatmospheric pressure and subsequent treatment with molecular oxygen containing gases in aqueous acetic acid by (a) separating the reaction mixture on the one hand into an aqueous phase containing cobalt acetate, pyridine, methylpyridines or mixtures thereof, acetic acid and methanol and on the other an organic phase containing methyl butanedicarboxylate, by-products, unconverted methyl pentenoate, acetic acid and also pyridine, methylpyridines or mixtures thereof, (b) extracting the organic phase obtained in step (a) with aqueous acetic acid to obtain an aqueous extract containing pyridine or methylpyridines or mixtures thereof as well as acetic acid, (c) combining the aqueous extract obtained in step (b) with the aqueous phase from step (a) and (d) isolating pyridine, methylpyridines or mixtures thereof by distillation from the aqueous solution produced in step (c) and obtaining a solution of cobalt acetate in aqueous acetic acid.

6 Claims, No Drawings

RECOVERY OF PYRIDINE OR METHYLPYRIDINES OR MIXTURES THEREOF FROM METHYL BUTANEDICARBOXYLATE CONTAINING REACTION MIXTURES

In the preparation of methyl butanedicarboxylates by reaction of methyl pentenoates with carbon monoxide and methanol in the presence of tertiary nitrogen bases, such as pyridine or methylpyridines, and cobalt carbonyl catalysts and subsequent treatment with molecular oxygen containing gases in aqueous acetic acid, as described in EP Application No. 10,581, aqueous cobalt acetate solution is recycled for catalyst synthesis while the organic phase is worked up by distillation. It has been found, however, that the tertiary nitrogen bases present in the reaction mixture, such as pyridine or methylpyridines, need to be separated off since otherwise the cobalt acetate solution obtained is highly contaminated.

It is an object of the present invention to recover from methyl butanedicarboxylate containing reaction mixtures pyridine, methylpyridine or mixtures thereof in reusable form and to obtain a cobalt acetate solution more suitable for catalyst synthesis.

We have found that this object is achieved with a process for recovering pyridine, methylpyridines or mixtures thereof from a methyl butanedicarboxylate containing reaction mixture obtained by reacting methyl pentenoate with carbon monoxide and methanol in the presence of pyridine, methylpyridines or mixtures thereof and a cobalt carbonyl catalyst at elevated temperatures and under superatmospheric pressure and subsequent treatment with a molecular oxygen containing gas in aqueous acetic acid, comprising (a) separating the reaction mixture into on the one hand an aqueous phase containing cobalt acetate, pyridine, methylpyridines or mixtures thereof, acetic acid and methanol and on the other an organic phase containing methyl butanedicarboxylate, by-products, unconverted methyl pentenoate, pyridine, methylpyridines or mixtures thereof as well as acetic acid, (b) extracting the organic phase obtained in step (a) with aqueous acetic acid to obtain an aqueous extract containing pyridine or methylpyridines or mixtures thereof as well as acetic acid, (c) combining the aqueous extract obtained in step (b) with the aqueous phase from step (a) and (d) isolating pyridine, methylpyridines or mixtures thereof by distillation from the aqueous solution produced in step (c) and obtaining a solution of cobalt acetate in aqueous acetic acid.

The novel process has the advantage that pyridine, methylpyridines or mixtures thereof are obtained in a simple manner in a reusable form and cobalt acetate solution in a form which is suitable for preparing cobalt carbonyl catalysts.

According to the invention, the starting point is a reaction mixture obtained by reacting methyl pentenoate with carbon monoxide and methanol in the presence of pyridine, methylpyridine or mixtures thereof and also cobalt carbonyl catalysts at elevated temperatures and under superatmospheric pressure and subsequent treatment with molecular oxygen containing gases in aqueous acetic acid. In general, mixtures of isomeric methyl pentenoates, in particular methyl 3-pentenoate, are present. Advantageously, the reaction is carried out using a molar ratio of methyl pentenoate:methanol of from 1:1.15 to 4, at from 140° to 200° C., in particular from 150° to 180° C., and under from 100 to 400 bar. Carbon monoxide is advantageously used in excess, for example in up to 10 times the stoichiometric amount. It has further proven to be advantageous if from 0.01 to 0.08 mole of cobalt carbonyl complex is present per mole of methyl pentenoate and from 2 to 10 moles of pyridine and/or methylpyridines per mole of cobalt catalyst. After letdown the reaction mixture obtained is advantageously treated with molecular oxygen or a molecular oxygen containing gas in aqueous acetic acid at pH 3-6 and at from 80° to 160° C. A suitable method for preparing the reaction mixture is described for example in EP Application No. 10,581.

The reaction mixture thus obtained is separated into on the one hand an aqueous phase containing cobalt acetate, pyridine or methylpyridines or mixtures thereof, acetic acid and methanol and on the other an organic phase which contains methyl butanedicarboxylate, by-products, acetic acid, pyridine, methylpyridines or mixtures thereof and unconverted methyl pentenoate. The separation is advantageously effected in a conventional manner, such as decanting, and advantageously at from 0° to 80° C.

The organic phase obtained in step (a) is extracted with aqueous acetic acid to produce an aqueous extract containing pyridine, methylpyridines or mixtures thereof as well as acetic acid. Should the amount of acetic acid present in the organic phase to be extracted not be sufficient, it is advantageous to ensure, by adding further acetic acid, that not less than 1 mole of acetic acid is present during the extraction per mole of pyridine and/or methylpyridine. Acetic acid can be employed in an excess of up to 10 moles. Preferably, the extraction is carried out in countercurrent in conventional extraction apparatus such as mixersettlers or sieve plate columns with or without pulsation. The extraction is advantageously carried out at from 10° to 80° C. using, advantageously, from 1 to 7 kg of aqueous acetic acid per kg of organic phase. Preferably, a bleed stream of the cobalt acetate containing aqueous acetic acid obtained in step d is used as extractant.

It has proven to be of particularly good utility to precede the extraction by distilling the organic phase to remove methyl butanedicarboxylate therefrom as a bottom product and to use in the extraction only the lower boilers which contain the pyridine, methylpyridines or mixtures thereof and also the pentenoic, valeric and isovaleric esters.

In step (c), the aqueous extract which contains acetic acid and pyridine or methylpyridines or mixtures thereof and, if the cobalt acetate solution from step (d) was used as extractant, cobalt acetate is combined with the aqueous phase from step (a), which contains cobalt acetate, pyridine and/or methylpyridines, mixtures thereof, acetic acid, methanol and possibly methyl acetate. Advantageously, the aqueous phase from step (a) is extracted beforehand with a suitable water-insoluble extractant, such as cyclohexane, in countercurrent, and the nonaqueous extract added to the organic phase of step (a).

In the aqueous solution resulting from step (c), which contains cobalt acetate, pyridine or methylpyridines or mixtures thereof, acetic acid, methanol and possibly methyl acetate is subjected in step (d) to a distillation to isolate pyridine and/or methylpyridines. Advantageously, first the low boilers methanol and methyl acetate are distilled off at the top of the column to leave an aqueous solution at the bottom of the column which contains cobalt acetate, acetic acid, pyridine and/or methylpyridines. This solution is preferably subjected to an azeotropic distillation with water to isolate pyridine and/or methylpyridine, leaving at the bottom of the column a purified aqueous solution of cobalt acetate and acetic acid. Advantageously, the water/pyridine and/or methylpyridine azeotrope is extracted with a water-insoluble organic extractant, such as benzene, toluene, xylenes, pyridine or methylpyridine or mixtures thereof. The remaining aqueous phase is recycled into the azeotropic distillation. The organic phase obtained, which contains pyridine or methylpyridines or mixtures thereof, extractants and small amounts of water, is subjected to distillation to remove the remaining water and extractant, leaving as the bottom product anhydrous pyridine or methylpyridines or mixtures thereof.

The process of the invention is illustrated in the following Example.

EXAMPLE

The starting point is a reaction mixture obtained by reaction of methyl 3-pentenoate with methanol and carbon monoxide in the presence of picoline and cobalt carbonyl and subsequent treatment with air and aqueous acetic acid. This mixture is separated in step a into an aqueous phase and an organic phase. The organic phase is distilled to remove methyl butanedicarboxylates as bottom products, and the low boilers are extracted as follows (Step b).

A pulsed sieve plate column is fed at 60° C. with 21.5 l/h of an organic pentenoic and valeric ester stream containing 13% (w/w) of β-picoline and 3% (w/w) of free acetic acid. The solvent introduced in countercurrent comprises 52 l/h of an aqueous cobalt acetate/acetic acid solution (from step d) containing 5.2% (w/w) of free acetic acid. A pulsation of 120 strokes/minute using about 5 theoretical plates leaves in the organic solution a residual picoline content of 0.7% (w/w), while the extract is found to contain 4.9% (w/w) of β-picoline.

The extract thus obtained is combined with the aqueous phase from step (a), which constitutes step c, and the combined phases are worked up as follows in step (d).

A 40-plate column is charged, onto the 28th actual plate, with an aqueous, cobalt acetate containing picoline solution at 80° C. in an amount of 762 g/h. The composition is 2.8% (w/w) of β-picoline, 0.18% (w/w) of methanol, 3.7% (w/w) of free acetic acid and 0.1% (w/w) of 3-pentenoic ester; the remainder is water. The picoline concentration in the top of column distillate is 19.7% (w/w) in addition to 0.6% (w/w) of 3-pentenoic ester and 3.4% (w/w) of methanol. This top of column product, obtained at a rate of 135 g/h, is extracted at 70° C. with 13.3 g/h of toluene to give 35 g/h of a toluene phase having a composition of 56% (w/w) of β-picoline, 25% (w/w) of toluene, 15.1% (w/w) of water, 2.1% (w/w) of methanol and 1.8% (w/w) of 3-pentenoic ester.

The aqueous reflux of 113.3 g/h still contains 7.5% (w/w) of β-picoline, 3.3% (w/w) of methanol and 0.06% (w/w) of toluene. The column is operated under atmospheric pressure, the top of column temperature is 97° C., and the bottom of column temperature is 103° C. The bottom runoff still contains 110 ppm of β-picoline.

A distillation column containing 9.4 m of Sulzer CY packing is charged at 30° C. at a packing height of 4.6 m, measured from the bottom, with 4.4 l/h of a mixture composed of 65.3% (w/w) of toluene, 27.6% (w/w) of β-picoline, 4.2% (w/w) of 3-pentenoic ester, 0.9% (w/w) of 2-trans-pentenoic ester, 1.4% (w/w) of water, 0.4% (w/w) of methyl valerate and 0.2% (w/w) of unknowns. Employing a 15 l/h reflux (toluene phase) at room temperature produces a bottom product of 89.8% (w/w) of β-picoline, 4.5% (w/w) of 3-pentenoic ester, 4.8% (w/w) of 2-trans-pentenoic ester and a water content of <0.02% (w/w). In the phase separator for the top of column product the toluene phase is found to contain picoline values <0.1% (w/w) and also about 1% (w/w) of ester. The column is operated under atmospheric pressure. The top of column temperature equilibrates to 110° C. and the bottom of column temperature to 145° C.

We claim:

1. A process for recovering pyridine, methylpyridines or mixtures thereof from a methyl butanedicarboxylate containing reaction mixture obtained by reacting methyl pentenoate with carbon monoxide and methanol in the presence of pyridine, methylpyridines or mixtures thereof and a cobalt carbonyl catalyst at elevated temperatures and under superatmospheric pressure and subsequent treatment with a molecular oxygen containing gas in aqueous acetic acid, comprising
   (a) separating the reaction mixture into on the one hand an aqueous phase containing cobalt acetate, pyridine, methylpyridines or mixtures thereof, acetic acid and methanol and on the other an organic phase containing methyl butanedicarboxylate, by-products, unconverted methyl pentenoate, acetic acid and also pyridine, methylpyridines or mixtures thereof,
   (b) extracting the organic phase obtained in step (a) with aqueous acetic acid to obtain an aqueous extract containing pyridine or methylpyridines or mixtures thereof as well as acetic acid,
   (c) combining the aqueous extract obtained in step (b) with the aqueous phase from step (a) and
   (d) isolating pyridine, methylpyridines or mixtures thereof by distillation from the aqueous solution produced in step (c) and obtaining a solution of cobalt acetate in aqueous acetic acid.

2. A process as claimed in claim 1, wherein in the extraction performed in step (b) not less than 1 mole of acetic acid is employed per mole of pyridine and/or methylpyridines.

3. A process as claimed in claim 1, wherein methyl butanedicarboxylate is separated off before the extraction of step (b).

4. A process as claimed in claim 1, wherein in step (d) methanol and methyl acetate are distilled off in a first distillation and pyridine or methylpyridines or mixtures thereof are then isolated in the form of an azeotrope with water.

5. A process as claimed in claim 1, wherein the water/pyridine and/or methylpyridine azeotrope obtained in step (d) is extracted with a water-insoluble organic extractant to remove pyridine and/or methylpyridines, the remaining aqueous phase is recycled into the azeotropic distillation to distill extractant and remaining water out of the organic phase and leaving anhydrous pyridine and/or methylpyridines as the bottom product.

6. A process as claimed in claim 1, wherein the aqueous cobalt acetate and acetic acid containing solution obtained in step (d) is used as an extractant in step (b).

* * * * *